(12) United States Patent
Barofsky et al.

(10) Patent No.: US 11,872,115 B2
(45) Date of Patent: Jan. 16, 2024

(54) POST-PARTUM HEMORRHAGE TREATMENT DEVICE

(71) Applicant: OBSTETRX, INC., Wilsonville, OR (US)

(72) Inventors: Andrew Barofsky, Wilsonville, OR (US); Mary Bullard, Wilsonville, OR (US)

(73) Assignee: OBSTETRX, INC., Wilsonville, OR (US)

( * ) Notice: Subject to any disclaimer, the term of this patent is extended or adjusted under 35 U.S.C. 154(b) by 917 days.

(21) Appl. No.: 16/874,440

(22) Filed: May 14, 2020

(65) Prior Publication Data

US 2020/0360192 A1    Nov. 19, 2020

Related U.S. Application Data

(60) Provisional application No. 62/847,462, filed on May 14, 2019.

(51) Int. Cl.
| | |
|---|---|
| *A61F 13/36* | (2006.01) |
| *A61F 13/20* | (2006.01) |
| *A61F 13/26* | (2006.01) |
| *A61F 13/34* | (2006.01) |
| *A61F 13/15* | (2006.01) |

(52) U.S. Cl.
CPC .......... *A61F 13/36* (2013.01); *A61F 13/2002* (2013.01); *A61F 13/2028* (2013.01); *A61F 13/2045* (2013.01); *A61F 13/2071* (2013.01); *A61F 13/266* (2013.01); *A61F 13/34* (2013.01); *A61F 2013/1517* (2013.01)

(58) Field of Classification Search
CPC .. A61F 13/36; A61F 13/2002; A61F 13/2028; A61F 13/2045; A61F 13/2051; A61F 13/2071; A61F 13/266; A61F 13/34; A61F 2013/1517
See application file for complete search history.

(56) References Cited

U.S. PATENT DOCUMENTS 3,821,350 A * 6/1974 Suchane ............. A61F 13/2082
                                                    264/259
5,383,891 A * 1/1995 Walker ............. A61F 13/00063
                                                    604/374

(Continued)

FOREIGN PATENT DOCUMENTS

WO    2011077145 A1    6/2011

*Primary Examiner* — Susan S Su
(74) *Attorney, Agent, or Firm* — Schwabe, Williamson & Wyatt, P.C.

(57) ABSTRACT

An intra-uterine device for treating post-partum hemorrhage (PPH) is described, along with an applicator system. In embodiments, the PPH device is comprised of a mesh pouch that is filled with a plurality of sponges. Each sponge is designed to expand upon absorption of fluids, such as blood. The collective expansion of the sponges within the mesh pouch causes the PPH device to expand within a patient's uterus, thus applying pressure to stanch blood flow. The PPH device is loaded into an applicator which is then inserted into a patient, and a corresponding plunger is used to deploy the PPH device. Following completion of treatment, the PPH device may be removed using a removal strand attached to the pouch that is exposed outside of the patient.

23 Claims, 6 Drawing Sheets

(56) References Cited

U.S. PATENT DOCUMENTS

| | | | |
|---|---|---|---|
| 6,315,763 B1* | 11/2001 | Albright | A61F 13/2051 604/385.18 |
| 8,828,050 B2 | 9/2014 | Gregory et al. | |
| 9,623,223 B2 | 4/2017 | Steinbaugh et al. | |
| 2009/0247928 A1* | 10/2009 | Bartning | A61F 13/266 604/15 |
| 2011/0077682 A1* | 3/2011 | Gregory | A61M 29/02 604/246 |
| 2012/0209232 A1* | 8/2012 | Barofsky | A61F 13/0233 156/196 |
| 2013/0110066 A1* | 5/2013 | Sharma | A61L 31/04 514/772.3 |
| 2014/0142523 A1* | 5/2014 | Steinbaugh | A61F 13/00051 604/374 |
| 2014/0316012 A1 | 10/2014 | Freyman et al. | |
| 2014/0316367 A1 | 10/2014 | Zugates et al. | |
| 2017/0020744 A1* | 1/2017 | Agrawal | A61F 13/2097 |
| 2017/0340488 A1 | 11/2017 | Miller | |
| 2019/0209389 A1* | 7/2019 | Jacobs | A61F 13/36 |

* cited by examiner

POST-PARTUM HEMORRHAGE TREATMENT DEVICE

This application claims the priority benefit of the earlier filing date of U.S. Provisional Patent Application No. 62/847,462, filed May 14, 2019, which is specifically incorporated herein by reference in its entirety.

FIELD

The present disclosure relates to hemostatic dressings useable in medical settings, and in particular, devices useable for managing post-partum and similar obstetrical bleeding or hemorrhaging.

BACKGROUND

Risks associated with pregnancy and childbirth present serious threats to the lives and well-being of women and children globally. Specifically, postpartum hemorrhage (PPH) is the leading cause of maternal mortality in low-income countries, and is responsible for a quarter of all maternal deaths globally. PPH is typically defined as a blood loss of 500 ml or more, within 24 hours of a birth. Uterine atony, or the ineffective contraction of the uterus following delivery, is responsible for the bulk of PPH cases. The majority of all deaths related to PPH will occur within 24 hours following delivery. Nearly all of these deaths could be prevented by timely and appropriate management.

DETAILED DESCRIPTION

Figure 1:
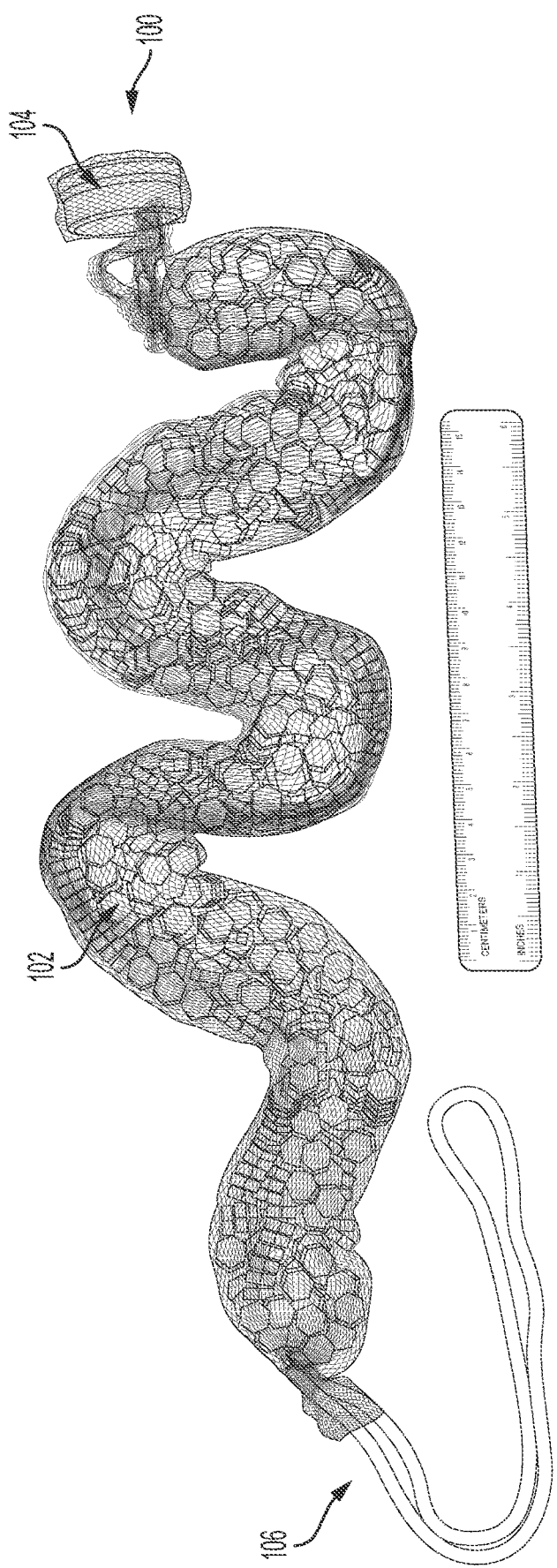
FIG. 1 is a top view of an example device for treatment of PPH, according to various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

PPH may be treated using a number of different techniques. For example, uterine tamponade is both an effective stabilizing treatment and an intermediate measure that can be implemented for reducing blood loss associated with childbirth. Various strategies have been utilized for uterine tamponade. These include uterine packing with sterile gauze, inflated foley catheters, condom catheters, and silicone obstetrical balloons. Case series data demonstrate the efficacy of these methods for reducing blood loss while preparing for definitive surgery. Despite the range of devices available, none is ideal. Effective packing with adequate amounts of sterile gauze is not readily accomplished by an inexperienced provider in a patient without an anesthetic. Deployment of a balloon catheter, while more effective, is a more complex procedure that requires a high degree of clinical skill and judgment. Although advances in training and the use of off-the-shelf dressings and devices have improved outcomes, there remains a need for a device to effectively treat PPH that can be reliably deployed by personnel with relatively little training.

Disclosed embodiments include a device and associated applicator to be used in addressing PPH. The disclosed PPH device embodiments can employ sponge technology effective to absorb blood and other bodily fluids from wounds while also expanding to apply pressure on a wound to stanch flow. The disclosed PPH device embodiments enclose a plurality of small sponges (i.e., "minisponges") in a porous pouch, designed to hold the plurality of sponges during insertion and removal, while allowing fluids to flow to and be absorbed by the plurality of sponges. The use of a pouch that encloses the plurality of sponges aids in rapid deployment and removal by allowing all sponges to be inserted in a single operation, rather that requiring a lengthy process of inserting and removing each sponge individually. The use of a plurality of sponges within a porous pouch, rather than a single or a few larger sponges, allows the sponges to assume the shape of and fill the uterine cavity when deployed, while deforming to the diameter of the cervix and vaginal canal to facilitate removal.

Notwithstanding the specific embodiments of sponges and associated materials described herein, a sponge may be implemented using any suitable liquid-expandable article or material, compatible with embodiments of the disclosed PPH device. "Liquid-expandable" refers to any material or substance that expands in occupied volume upon contact with a liquid. Once expanded, a liquid-expandable article, such as a sponge, may be soft and pliable. Without being limited to any particular theory, this quality may permit the liquid expandable articles to conform to irregular wound crevices, gaps, and fissures. Further, by use of a plurality of relatively small sponges, e.g. minisponges, as will be described in greater detail herein with respect to various embodiments, the overall shape can change and conform as the plurality of sponges move relative to each other in the disclosed PPH device embodiments.

In FIG. 1, the components of an example PPH device 100 are depicted. Example PPH device 100 includes a roughly tubular pouch 102, a tip 104 disposed on a first end of pouch 102, and a removal strand 106 disposed on a second end of pouch 102 that is distal from the first end. Pouch 102, in the depicted embodiment, is filled with a plurality of sponges 108. The roughly tubular, or elongated, nature of pouch 102 helps facilitate removal of pouch 102 through a potentially contracted cervix following expansion of sponges 108. In one possible embodiment, the sponge pouch 102 is composed of a porous, expandable pouch (4.5 cm flat width×80 cm length) that contains approximately 300 compressed cellulose sponges. The pouch 102, in some embodiments, is a tubular knit woven textile constructed with a medical-grade ultra-high molecular weight polyethylene (UHMWPE) fiber.

Pouch 102 is typically sized, in embodiments, with respect to the amount and type of sponges 108 enclosed within pouch 102. Pouch 102, in the depicted embodiments, is an elongated tube, with a length that is greater than its cross section. Pouch 102 may be roughly circular or ovoid in cross section. The cross section, in embodiments, is sized to be easily received through the cervix of an uncontracted uterus, and to fit within the body of an applicator, discussed below. The elongated length of pouch 102, in embodiments, is selected to provide an optimal sponge density, which will maximize absorption and pressure to stanch blood flow while still allowing the PPH device 100 to be comfortably extracted from the patient's uterus. In various embodiments, the pouch may range in flat width from 1 cm to 15 cm, and in length from 25 cm to 150 cm. These dimensions should be taken as example ranges and not necessary limits; other dimensions outside of these ranges may be possible for a given implementation, provided the length exceeds the flat width. The selection of the specific width and length for a given pouch 102 will depend upon a given patient, the selection and properties of sponges 108 to fill pouch 102, and the way in which the dimensions of pouch 102 will change as the sponges 108 expand (discussed in greater detail below). For example, in the embodiment described above, pouch 102 is approximately 4.5 cm flat width by 80 cm in length (that is, empty and prior to being filled with sponges).

In the example embodiment of pouch 102, pouch 102 will hold approximately 300 compressed sponges 108, the sponges 108 of a nominal diameter of 9.8 mm and a compressed height of 4-5 mm. Where such sponges are fabricated from compressed cellulose, this results in a sponge density of approximately 10+/−3 sponges per 2.5 cm of pouch length, or expressed in weight, 1.6 g of sponge for each 2.5 cm of pouch length, or a density of 0.64 g/cm. In various embodiments, a range of densities between 0.45-0.83 g/cm may be employed. In other embodiments, a density as low as 0.2 g/cm may be employed, with an upper range of 1 g/cm. These densities have been empirically determined for sponges 108 fabricated from cellulose. Employing different types of sponge material and/or different sponge sizes or shapes may necessitate different dimension to pouch 102 to achieve the aforementioned optimal sponge density. Further, the density may deviate from these ranges for a given pouch, in various embodiments, depending upon the selection of materials and/or configuration for sponges 108. For example, where sponges 108 are manufactured from a material that is more dense than cellulose, a density exceeding 1 g/cm may yield acceptable results, while sponges 108 manufactured from a material that is less dense than cellulose may yield acceptable results with a density less than 0.2 g/cm. It will be appreciated by a person skilled in the art that the number of sponges mentioned above is an approximate number, as the actual number of sponges inserted into pouch 102 may vary due to variations in the sponge material and dimensions. Furthermore, PPH device 100 may vary in size in embodiments to accommodate patients of different sizes, resulting in further variations in the number of sponges. In some embodiments, the number of sponges may range from 250 to 350. Other embodiments may have from 295 to 305 sponges, from 290 to 310 sponges, from 275 to 325 sponges, from 200 to 400 sponges, from 100 to 500 sponges, from 1 to 500 sponges, a range between any of the foregoing, another range of numbers outside the foregoing ranges, or at least one sponge, particularly in embodiments where the length and/or cross section of pouch 102 may vary.

In still other embodiments, pouch 102 may be separated into two or more compartments or sections. One, more than one, or all compartments may be filled with sponges 108. In some embodiments, a first compartment may be filled with a first type of sponge 108, and a second compartment may be filled with a second type of sponge 108. In embodiments where pouch 102 has more than two compartments, some of the compartments may be filled with a first type of sponge 108, and other compartments may be filled with a second or additional types of sponge 108. In further embodiments, all compartments may be filled with the same sponge 108. In some embodiments, the compartments may be of the same or different sizes, and/or may be filled with sponges 108 to different sponge densities, or the same sponge density. Some embodiments may include combinations of any of the foregoing.

The textile of pouch 102, as depicted, is essentially a mesh material that allows fluids (such as blood from a PPH) to be readily passed to each of the sponges 108. Further, the textile may be distensible in nature, in embodiments, to accommodate the expansion of the various sponges 108 as they absorb fluids while presenting minimal to no resistance against the sponges 108 as they expand. Thus, with a distensible material, the sponges 108 are not prevented from achieving substantially maximum expansion by the pouch 102. In various embodiments, pouch 102 may exhibit a positive Poisson's ratio, radially narrowing (viz. decreasing in area of cross section), particularly around its central region (e.g., the region between each end of the pouch 102), when the pouch 102 is stretched lengthwise, and similarly shortening lengthwise as pouch 102 is radially expanded, e.g. when the sponges 108 absorb fluid and expand to fill the pouch 102. This positive Poisson's ratio behavior can allow PPH device 100 to absorb fluid and expand to provide the aforementioned stanching effect when placed within a uterus, while narrowing when stretched during the removal process to allow the PPH device 100 to pass through a narrow or contracted cervix. In embodiments, the expansibility of pouch 102, particularly in embodiments using a distensible material, may be achieved by selection of construction of the pouch textile. For example, some embodiments may utilize a tubular weft knit. Other embodiments may additionally or alternatively introduce folds in the porous textile material. In embodiments of pouch 102 that use distensible material, the fibers themselves may be manufactured from a low elasticity material, or a non-elastic material, such as ultra high molecular weight polyethlyene (UHMWPE), which also provides relatively high strength and high lubricity (e.g. low friction) properties.

In other embodiments, the pouch 102 may utilize an elastic material. In such embodiments, the degree of elasticity of the textile may be selected to control the degree of expansion of the sponges 108 and/or the overall expansion of the PPH device 100 to a predetermined and/or desired amount. For some such embodiments, the textile may or may not be inherently elastic in nature, depending upon the desired distensible or elastic properties. Other embodiments may employ different types of textiles and/or different textile materials, with varying characteristics such as permeability and elasticity/expansion, as suitable for medical use and/or appropriate to a particular embodiment. For example, textile materials may comprise one or more low friction materials to facilitate deployment of pouch 102 from applicator 300 and high tensile strength to facilitate removal of pouch 102 through a contracted cervix following expansion of sponges 108 without tearing.

Optional removal strand 106, in embodiments including a removal strand, is a 1-cm×20-cm woven cotton strand, attached to the pouch to facilitate post-treatment removal. Other materials capable of withstanding the stresses imposed by removal may instead be used for removal strand 106, such as a suitable medically safe synthetic material like nylon, polyester, polypropylene, etc. The length of removal strand 106 may also vary in some embodiments, or be modified to as necessary for a given patient/implementation. Removal strand 106 may be attached to pouch 102 (specifically, the second end of pouch 102) in any sort of secure fashion that will withstand the tension forces imposed upon removal strand 106 during the removal of PPH device 100, without separating from pouch 102 or tearing, either removal strand 106 or pouch 102. Removal strand 106 may be secured using sewing, adhesives, sonic welding, or another suitable attachment method. The size and/or material of removal strand 106 as well as the mechanism by which removal strand 106 is joined to pouch 102 may be selected with respect to the size of a given PPH device 100.

The first end of the pouch may optionally contain a tip 104, in embodiments, that serves as the applicator tip and helps prevent fluid ingress into the sponges 108. In various embodiments tip 104 is enclosed inside pouch 102. For such embodiments, pouch 102 may be separated into two or more compartments (such as described above), wherein tip 104 may be enclosed in one compartment and the sponges enclosed separately in the other compartment or compartments. In other embodiments, tip 104 is secured or attached to the outside of pouch 102, such as a first end of a tubular pouch 102 that is opposite from a second end to which a removal strand 106 may be attached. In various embodiments tip 104 comprises a rubber or cork-like material. In some embodiments, tip 104 comprises uncompressed sponge, which may be highly conformable and/or compliant when wetted, which can ease removal through a contracted cervix. In other embodiments tip 104 comprises compressed sponge. For other embodiments, tip 104 may alternatively or additionally employ lamination, or another surface coating, in part to prevent the sponge tip from expanding during insertion. The core of tip 104 may be made from any suitably absorbent, medically safe material or materials that can help facilitate easy deployment within a patient, while preventing excessive fluid from reaching the sponges 108 during deployment that may cause premature expansion and prevent proper deployment. As depicted in the embodiment of FIG. 1, the tip 104 has a roughly dome shape. Other embodiments may employ a different shape, depending upon the application mechanism and/or technique, patient considerations, and any other pertinent concerns for a given implementation. Embodiments that employ an uncompressed, unlaminated sponge may provide sufficient comformation or compliance, particularly when wetted, to facilitate a relatively easy removal through a contracted cervix. In still further embodiments, the dome portion of tip 104 comprises compressed sponge, and the non-dome portion comprises un-compressed sponge.

Figure 2:
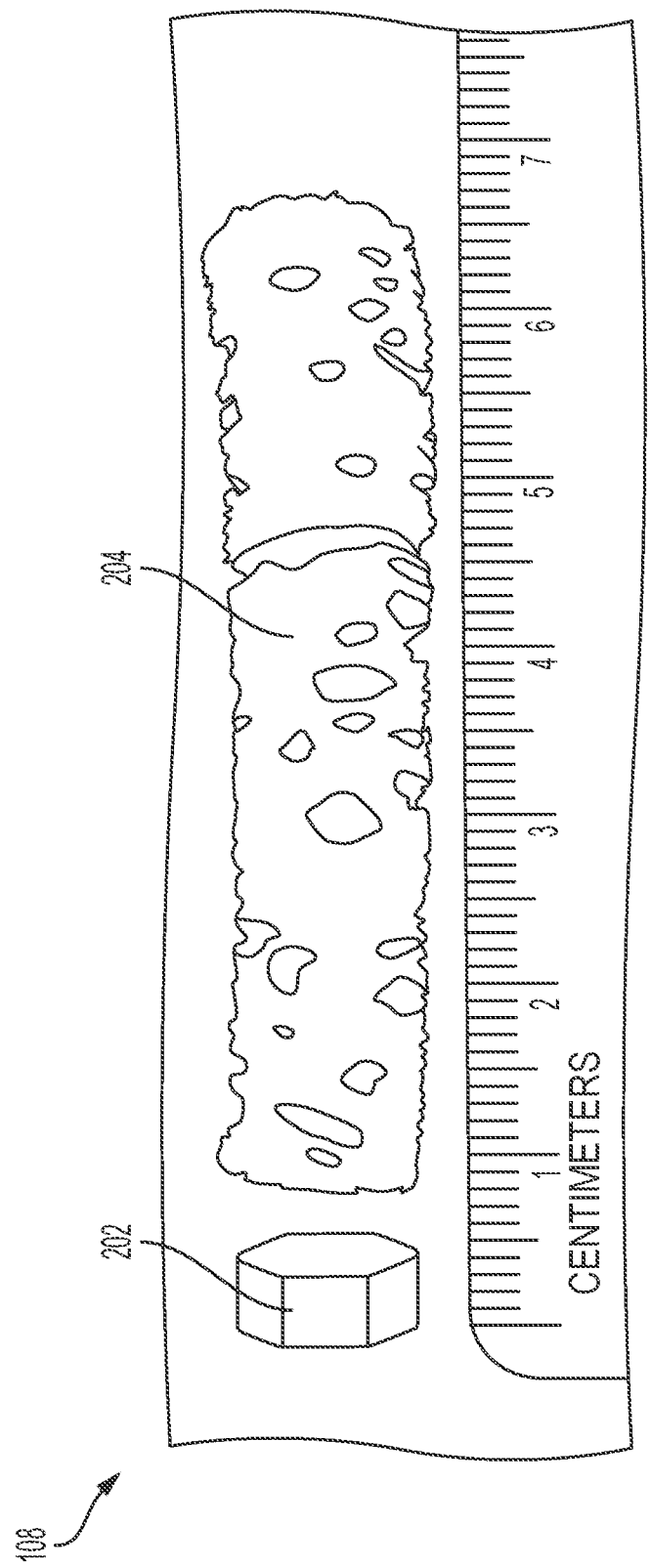
FIG. 2 is a side view of an example sponge that may be contained within the PPH device depicted in FIG. 1, according to various embodiments.

In FIG. 2, one of the sponges 108 is depicted, according to some embodiments. In embodiments, each sponge 108 is made from a liquid-expandable material or materials. As used herein, "liquid-expandable" means a material that expands upon contact with a liquid. The material is considered "pre-expanded" when still in a dry, possibly compressed, form prior to contact with a liquid. In some embodiments, each sponge 108 is made from a cellulose material. In other embodiments, other suitable materials may be used, such as starch, chitin, or chitosan material. In other embodiments, each sponge 108 may be constructed from another medically safe liquid-expandable material or combination of materials that allows the sponge 108 to achieve a desired dimensional expansion, such as a natural or synthetic material. In still other embodiments, rather than a sponge or similar structure, sponges 108 may be implemented using another form factor of absorbent material, such as beads, prills, a power, or another medium that can be retained within pouch 102 in both dry and wet form. The selection of the form factor may be influenced by the construction and configuration of pouch 102.

One or more sponges 108 are placed into pouch 102 in a compressed form 202, and remain in the compressed form 202 until insertion. In some embodiments of PPH device 100, each sponge 108 within pouch 102 may be manufactured from the same material. In other embodiments, sponges 108 may be made from a variety of different materials, to achieve a desired effectiveness of PPH device 100. Following insertion, each sponge 108 may begin absorbing fluid, e.g. blood and sera, which causes each sponge 108 to expand to an expanded form 204. In some embodiments, expanded form 204 is approximately ten times the length of the compressed form 202, while not appreciably expanding in width. In the particular embodiment depicted in FIG. 2, each sponge 108 has a circular surface diameter of 9.8 mm and is compressed to an initial height of 4-5 mm. Other embodiments may vary the diameter, such as between 9 and 10 mm, 7 and 12 mm, 5 and 14 mm, or another suitable range. Each sponge 108 may be cut into a hexagonal shape. Upon contact with blood, each sponge 108 absorbs blood and, if unencumbered, expands to a pre-compressed height (e.g. expanded form 204) of 40-50 mm within approximately 20 seconds. Other embodiments of sponges 108 may expand to a different size and/or at a different rate, e.g. 5, 10, 15, 25, 30 or more seconds, depending upon the geometry and/or material(s) used to fabricate the sponge 108. The sponge 108 in the depicted embodiment expands only in length, not width. Other embodiments may employ sponges of different compressed form 202 and expanded form 204 dimensions, which may further expand in multiple dimensions, e.g. increasing in width as well as length.

The time over which sponge 108 expands from its pre-expansion, unwetted form factor to a post-expansion, fully absorbed form factor may be selected with respect to a desired therapeutic outcome, e.g., how quickly the PPH device 100 is to expand within a uterus and stanch any blood flow. The speed of expansion may impact the amount of stanching force ultimately applied by PPH device 100. In some embodiments, a relatively rapid speed, e.g. less than one minute following exposure to fluid, is desirable to achieve a rapid stanching of flow. In other embodiments, a slower or more gradual expansion may be desirable. In still other embodiments, a mixture of sponges 108 with varying expansion rates may be employed, with faster expanding sponges 108 providing a rapid initial stanching, and slower expanding sponges 108 providing continued, slower absorption of fluids that may continue to seep if the initial stanching is insufficient, thereby increasing the stanching pressure.

In various embodiments, the plurality of sponges 108 located within pouch 102 may all be uniform in size, or may comprise a mixture of sizes. In an embodiment, each sponge 108 may have the same diameter, but may have different lengths. Alternatively, the diameters may vary among the sponges 108. Combinations of the above are also provided.

According to various embodiments, an expanded sponge 108 occupies a volume greater than a compressed sponge 108. In various embodiments, the average volume ratio of each compressed sponge 108 to an expanded sponge 108 is at least 4×. In other embodiments, the average volume ratio of each compressed sponge 108 to expanded sponge 108 is at least 8×. In other embodiments, the average volume ratio of a compressed sponge 108 to expanded sponge 108 is at least 10×. In other embodiments, the average volume ratio of a compressed sponge 108 to expanded sponge 108 is at is at least 12×.

Sponges 108 may vary in absorption capacity depending upon size, shape, and material. Sponges 108 may range in pre-expansion volume from 0.7 mm$^3$ to 7000 mm$^3$, or may have a pre-expansion volume of a lesser or greater amount, depending upon the needs of a given embodiment. The pre-expansion volume may impact the speed at which each sponge 108 reaches full expansion and/or the ultimate pressure that PPH device 100 may impart to the uterus for stanching flow. In various embodiments, each sponge 108 may be capable of expanding to 80% or greater of its maximum expansion capacity in 60 seconds or less following immersion in liquid. In other embodiments, each sponge 108 may be capable of expanding to 80% or greater of its maximum expansion capacity in 30 seconds or less following immersion in liquid. In other embodiments, each sponge 108 may be capable of expanding to 80% or greater of its maximum expansion capacity in 10 seconds or less following immersion in liquid. In other embodiments, each sponge 108 may be capable of expanding to 80% or greater of its maximum expansion capacity in 5 seconds or less following immersion in liquid.

The plurality of sponges 108 may comprise one or more predetermined shapes, based on adjustments to the length, width, diameter, or cross-sectional shape. Without being limited by theory, the shape, size and/or pattern of each sponge 108 may influence the ability of the PPH device 100 to fit into, expand, fill, partially fill and conform to a uterine cavity. In addition, the shape may assist the PPH device 100 in retaining a desired position in the uterus.

In FIG. 2, each sponge 108 is depicted as a cylindrical shape with a hexagonal cross-section. This notwithstanding, the predetermined shape of each sponge 108 may include round, triangular, rectangular, hexagonal, conical, or octagonal cross-sections. In various embodiments, sponges 108 multiple projections (e.g., a star) may be used. In other embodiments, PPH pouch 100 may include a plurality of sponges 108 with haphazard, random, irregular, or jagged shapes. In various embodiments, PPH pouch 100 may include a plurality of sponges 108 with two or more predetermined shapes. In other embodiments, PPH pouch 100 may have sponges 108 comprising a mixture of predetermined shapes and/or irregular shapes.

In various embodiments, the sponges 108 may comprise an absorbent material including, but not limited to, a sponge or fibrous material. In various embodiments, the absorbent material may comprise a polysaccharide such as, but not limited to, cellulose, starch, chitin, or chitosan. In various embodiments, sponges 108 may be biodegradable and/or bio-absorbable. In some embodiments, the sponges 108 may comprise non-oxidized cellulose. In various embodiments, the absorbent material may comprise synthetic sponges such as, but not limited to, various polyvinyl alcohol (PVA) polymers and derivatives thereof having desirable physical and mechanical properties.

Relevant disclosure concerning sponges 108 and similar devices is provided in U.S. Pat. No. 8,828,050, the entirety of which is hereby incorporated by reference as if fully stated herein.

Figure 3:
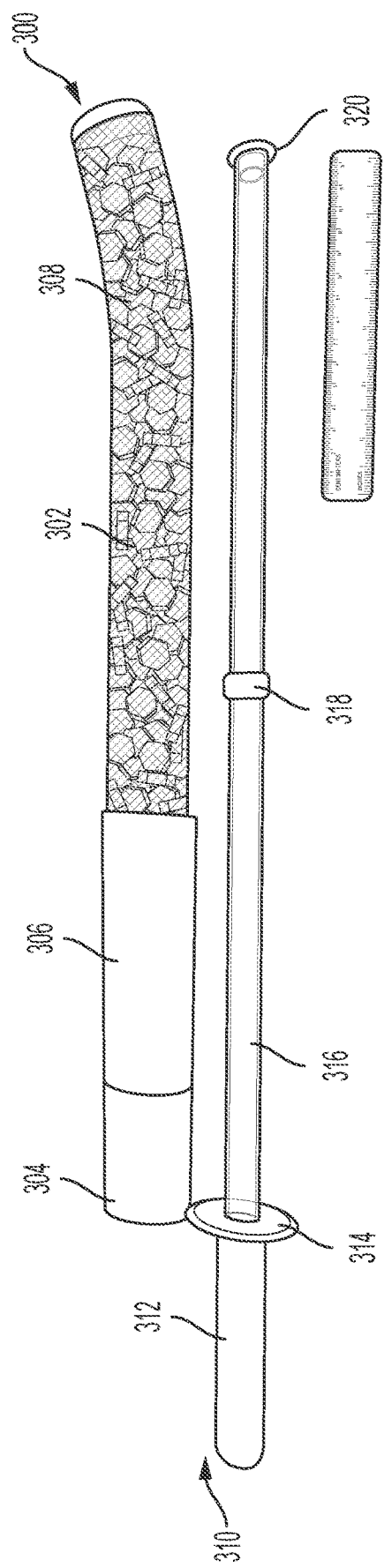
FIG. 3 is a top view of the PPH device of FIG. 1 contained within an example applicator and alongside an example plunger for deploying the PPH device, according to various embodiments.

In FIG. 3, an applicator system is depicted, including an applicator 300 along with a plunger 310, to use in conjunction with applicator 300 for deployment of PPH device 100. Applicator 300, in the depicted embodiment, includes an applicator body 302, an end cap 304 to interface with plunger 310, and a grip 306 that joins between applicator body 302 and cap 304. Other embodiments may include more or fewer components.

In other embodiments, applicator 300 may include a valve coupled to the applicator body 302 at the end of the applicator body 302 that is distal from end cap 304. The valve may be employed as an alternative, or in addition to, tip 104 to prevent the premature exit of pouch 100 from applicator body 302, as well as impede the flow of liquid into applicator body 302 prior to the ejection of pouch 100, such as during application to a patient.

Near the end of the applicator body 302 that is distal from end cap 304 is a curve 308 of a suitable angle to help assist in the insertion of applicator 300 into a patient for deployment of PPH device 100. In the depicted embodiment, the applicator body 302 is a 29 mm outer diameter×38 cm length tubing with a curvature at the distal end to facilitate access into the lower uterine segment; the grip 306 is 8 cm long and may partially or fully overlay a portion of applicator body 302; and low-density polyethylene (LDPE) cap 304 is configured to engage (e.g. "clicks" into) plunger 310. In embodiments, applicator body 302 has a substantially round cross section. In other embodiments, applicator body 302 may have an oblong or ovoid cross section, a polygonal cross section, or a complex or variable cross section depending upon the needs of a given implementation. Applicator body 302 has a cross section area sized to enclose PPH device 100 in its dry, e.g. unexpanded state, with an outer diameter small enough to insert into the patient's cervix. The outer diameter may, in embodiments, vary to accommodate patients of different sizes. As seen in FIG. 3, prior to application, the PPH device 100 is inserted into applicator 300, with the sponge pouch 102 portion housed inside the applicator body 302, and tip 104 exposed at one end of applicator body 302.

As illustrated in the embodiment of FIG. 3, the curve 308 may be located more proximate the end of applicator body 302 that is inserted into the patient, and may have a relatively wide radius. Other embodiments may vary where the curve 308 begins on applicator body 302 and/or may vary the radius, such as to accommodate differing patient anatomies and/or sizes, or to adjust comfort for a particular patient. Still other embodiments may construct applicator body 302 from a semi-flexible material that allows the location and/or radius of curve 308 to be adjusted on the fly by a user of the applicator 300, or possibly to support more complex curves (e.g. multiple bends in three dimensions). Applicator body 302 is open at its end distal from cap 304, in embodiments, to expose tip 104 for application, and further to provide an aperture through which PPH device 100 will pass into a patient's uterus when deployed.

Cap 304 may be provided to retain removal strand 106 within applicator 300. In some embodiments, cap 304 may be removed prior to application of PPH device 100 into a patient, to expose removal strand 106. In other embodiments, cap 304 may be retained in place, and provide an interior aperture through which plunger 310 may be inserted for deployment of PPH device 100. Such an aperture may facilitate proper location of plunger 310 with respect to PPH device 100, to ensure that the plunger pushes PPH device 100 centrally and minimize the possibility of PPH device 100 being improperly deployed. Other embodiments may have cap 304 engage with and lock to plunger 310, such as tip 320, where a portion or all of cap 304 may act as a plunger to deploy PPH device 310. As mentioned above, cap 304 may be constructed from low-density polyethylene (LDPE), in embodiments. Other embodiments may construct cap 304 from other suitable materials, such as nylon or another (medically safe) suitable material.

In some embodiments cap 304, regardless of whether acting as a plunger, may be temporarily secured to removal strand 106 to retain it within applicator body 302 as PPH device 100 is inserted into a patient. Removal of cap 304 from applicator body 302 in such embodiments will allow the removal strand 106 to be detached, with an end of removal strand 106 exposed either outside the patient or within the vaginal canal for subsequent removal of a deployed PPH device 100. This will be discussed in greater detail below with respect to FIG. 4.

Sleeve or grip 306 is provided, in embodiments, to provide a useful location for a user of applicator 300 to grip the applicator 300 and manipulate it during deployment of PPH device 100 into a patient. In some embodiments, grip 306 may be configured with a textured surface to facilitate handling. In some embodiments, grip 306 comprises a sleeve coupled to applicator body 302. For such embodiments, grip 306 may be manufactured from vinyl. In other embodiments, grip 306 may be manufactured from a material other than vinyl; any suitable material that allows a user to reliably grip applicator 300 during deployment of PPH device 100 may be employed. In other embodiments, grip 306 may be created by texturizing the surface of applicator body 302. The size of grip 306 may vary depending upon the specific needs of a given implementation of applicator 300.

Applicator body 302 may be manufactured from any suitable medically safe material that can withstand the forces imposed upon applicator 300 during the insertion of a PPH device 100 within a patient. In some embodiments, applicator 300 is a single use device along with PPH device 100, and so may be constructed from a suitable plastic or other (relatively) cheap and/or disposable or recyclable material. Likewise cap 304 may be constructed from a plastic or another suitable material that can withstand any forces that may be imposed upon the cap during application of the PPH device 100.

Plunger 310, in the depicted embodiment, includes a hand grip 312, a hilt 314, a plunger tubing 316, a finger grip 318, and a tip 320. Other embodiments may include additional components, or omit one or more of the foregoing components, such as the finger grip 318. Hand grip 312 is to be gripped by a user of applicator 300 to provide pressure into applicator 300 for deploying PPH device 100 into a patient. Hand grip 312 may be of a somewhat larger diameter from plunger tubing 316, and/or may be contoured to provide a more sure grip for a user of plunger 310. In some embodiments, hand grip 312 may further include a textured surface. Hand grip 312 may be manufactured from any suitable material that can be sterilized or sanitized.

Hilt 314, in embodiments, can act as a stop to prevent a user of applicator 300 from over-inserting plunger 310 and/or PPH device 100, which may otherwise cause internal injury to a patient. Hilt 314 thus may be sized at least as large as, or larger than, the diameter of applicator body 302 and/or cap 304 or grip 306, to prevent over-insertion. In other embodiments, such as where applicator 300 is relatively fully inserted into a patient's vaginal canal, hilt 314 may be of sufficient size so as to prevent insertion past the vaginal opening. Hilt 314 may be manufactured from any suitable material that can be sterilized or sanitized.

Plunger tubing 316 comprises the body of plunger 310, and is designed to transmit the force from a user to PPH device 100 as it is deployed from applicator 300. In the depicted embodiment, plunger tubing 316 is substantially round, and is manufactured from a material and to such dimensions so as to render plunger 310 sufficiently rigid to transmit the force necessary to deploy PPH device 100 from applicator 300. Such materials may include, but are not limited to, plastic or metal, or any other suitable material that can be sterilized or sanitized. It will also be observed that, in the depiction in FIG. 3, the length of plunger 310 measure from hilt 314 to tip 320 is just short of the overall length of applicator 300. This length may be selected relative to the length of applicator 300 to ensure that PPH device 100 is reliably deployed, but to prevent plunger 310 from extending past the end of applicator 300 (via interaction with hilt 314), where it could otherwise cause internal injury to the patient. Further, as plunger tubing 316 may be substantially straight and rigid, the diameter of plunger tubing 316 may be sized to accommodate the curve 308 of applicator body 302 without binding or otherwise interfering with the positioning of applicator body 302. Further still, curve 308 may be configured with consideration of the size of plunger tubing 316.

Finger grip 318, in embodiments equipped with a finger grip, provides an additional point with which a user of plunger 310 may grip plunger 310 for better control when positioning plunger 310 into applicator 300. Finger grip 318 may be located approximately at the midpoint of plunger tubing 316 between hilt 314 and tip 320, in some embodiments, or may be located more proximate to either hilt 312 or tip 320 depending upon the needs of a given implementation. In still other embodiments, finger grip 318 may be moveable longitudinally along plunger tubing 316 to any position desired by a user of plunger 310. Finger grip 318 may be manufactured from any suitable material that can be sterilized or sanitized.

Finally, tip 320, in some embodiments, engages with cap 304 to act as the plunger to push PPH device 100 from applicator 300 into a patient. In such embodiments, tip 320 may be configured with protrusions, notches, slots, or some other mechanical contrivance to allow it to engage with a corresponding contrivance on cap 304. In other embodiments, tip 320 may itself act as the plunger, and either pass through cap 304, or through the end of applicator body 302 in embodiments where cap 304 is removed prior to use. Tip 320 may be manufactured from any medically compatible and suitable material that can be sterilized or sanitized.

Figure 4:
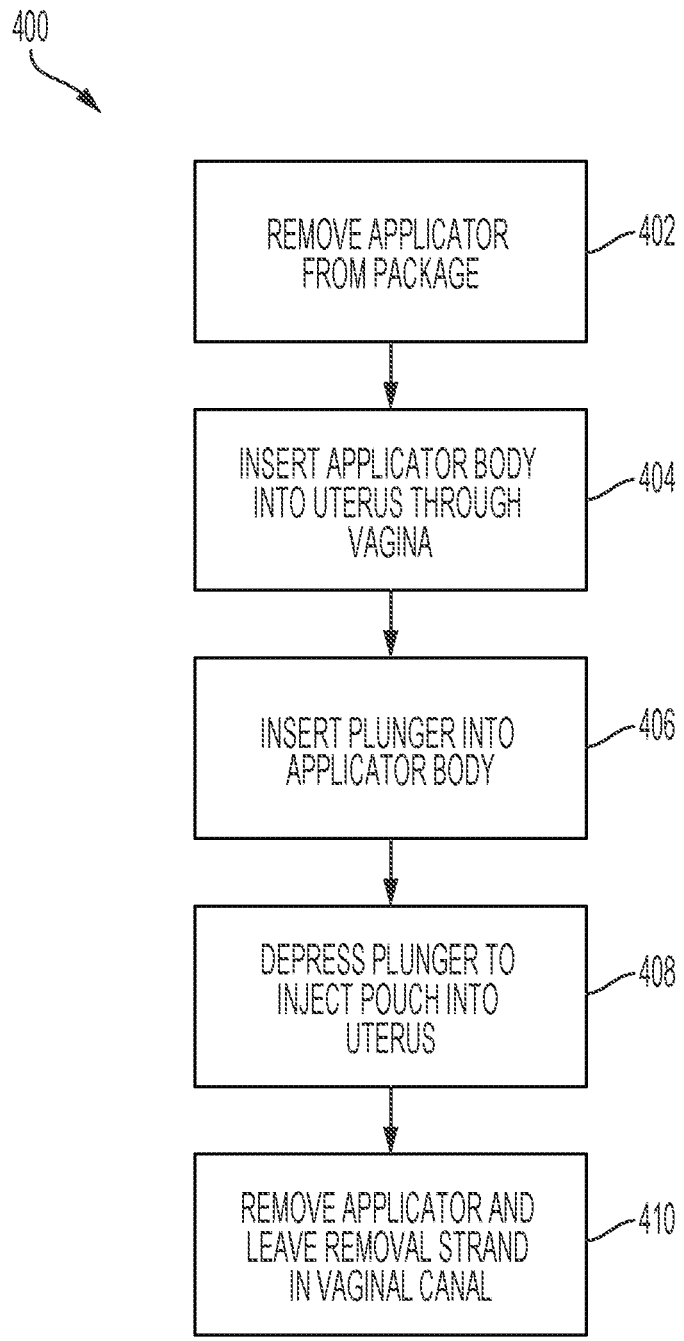
FIG. 4 is a flowchart of possible actions to deploy the PPH device of FIG. 1 using the applicator and plunger of FIG. 3, according to various embodiments.

In FIG. 4, the operations of an example method 400 for deploying the PPH device 100 are depicted. Method 400 may be performed in whole or in part with PPH device 100, applicator body 300, and plunger 310. For the treatment of uterine bleeding during postpartum hemorrhage, the PPH device 100 is applied as follows: First, in operation 402, the applicator 300 and plunger 310 are removed from a sealed package that was previously sanitized, such as via gamma irradiation or another suitable sterilization method. In other embodiments, applicator 300 and plunger 310 may be located in separate sterilized or sanitized packages. In some embodiments, PPH device 100 may be first assembled by filling the pouch 102 with sponges 202 to an amount appropriate to achieve the desired sponge density. Following filling, the PPH device 100 may need to be sterilized, if filling was not able to be accomplished in a sterile environment.

In operation 404, the applicator body 302 of applicator 300 is inserted through the patient's vagina and into the patient's uterus, making certain that the applicator tip with tip 104 is inserted past the cervical canal and internal ostium. The user of applicator 300 may use the grip 306 to assist in positioning applicator 300. The curve 308 may be positioned to follow the natural shape of the patient's cervix and uterus.

In operation 406, the plunger 310 is inserted into the applicator body 302. As discussed above, in some embodiments, tip 320 of plunger 310 is engaged with cap 304, which acts as the plunger. In other embodiments, tip 302 of plunger 310 itself acts as the plunger, with cap 304 either being removed (such as where cap 304 closes the end of applicator body 302) or acting to center plunger 310 that passes through cap 304.

In operation 408, the plunger is depressed to inject the sponge pouch 102 of PPH device 100 into the uterus. In some embodiments, the plunger is depressed until physically stopped by hilt 314, which may be positioned to ensure that, provided applicator 300 is correctly positioned within the patient, full insertion to hilt 314 will result in a properly deployed PPH device 100.

Finally, in operation 410, the applicator 300 is gently removed from the uterus, and the removal strand 106 is left in the vaginal canal. In some embodiments, removal strand 106 extends past the vaginal canal to outside of the patient, as depicted. In other embodiments, removal strand 106 stays within the patient in the vaginal canal. The removal strand 106 may either be shortened to a desired length (inside or outside the vaginal canal), such as by cutting, or may be preconfigured to a desired length. As discussed above, the free end of removal strand 106 may be removably attached to cap 304. Removal of cap 304 from applicator 300 thus frees the end of removal strand 106 to either within the vaginal canal or outside the patient, where it remains to facilitate later removal of PPH device 100. Once inside the uterus, the sponges 108 absorb blood and expand the pouch, thereby packing the uterus and stanching blood flow.

Once the PPH device 100 has been in place for a suitable amount of time, e.g. when blood flow has been stanched and possibly when the uterus has contracted, PPH device 100 may be removed by gentle pulling on the removal strand 106, discussed below with reference to FIG. 7. The selection of sponges and dimensions of pouch 102 to achieve an optimal sponge density allows the PPH device 100, which may have coiled and/or folded to fill the uterus, to uncoil/unfold and be readily removed through a contracted cervix with minimal to no discomfort to the patient.

Figure 5:
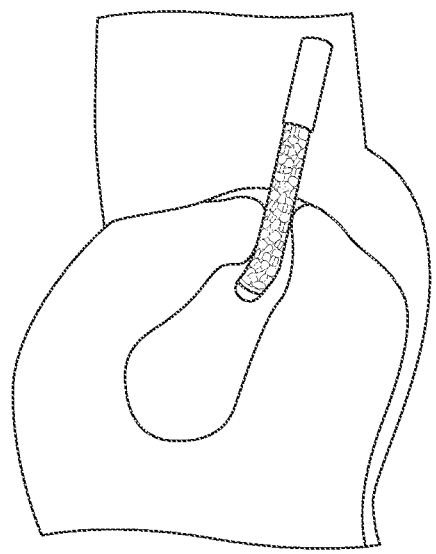
FIG. 5 is a diagram of the positioning of the PPH device of FIG. 1 and applicator for deployment, according to various embodiments.

FIG. 5 depicts the positioning of an applicator body 300, including an enclosed PPH device 100, within a patient to be treated for PPH. As seen, the tip 104 is inside the patient's uterus, with the curve 308 of applicator body 302 positioned approximately about the cervix. The position depicted in FIG. 5 is pre-insertion of PPH device 100, and corresponds to the completion of operation 404 of method 400.

Figure 6:
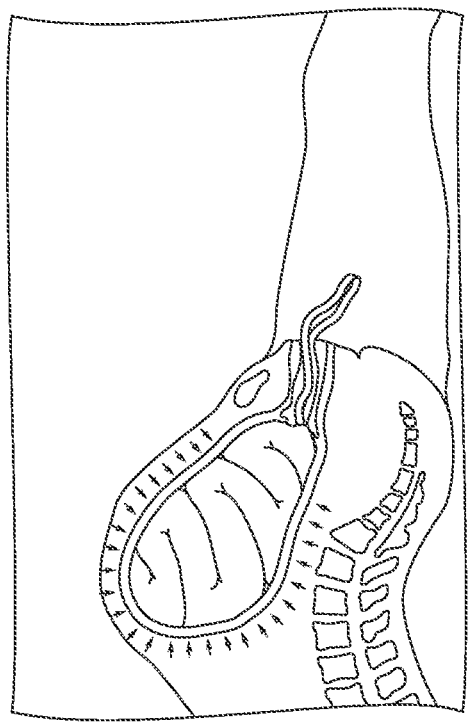
FIG. 6 is a diagram of the PPH device of FIG. 1 in a deployed configuration, according to various embodiments.

FIG. 6 depicts the PPH device 100 as deployed within a patient, following completion of the entirety of method 400 through operation 410. As can be seen, the tube-like PPH device 100 may fold or coil to fit within the uterus, and fill the entire uterus following expansion. Further, FIG. 6 also depicts the result of PPH device 100 having absorbed sufficient fluids, e.g. blood, to cause at least the majority of the sponges 108 to expand and thus cause PPH device 100 to expand and fill the patient's uterus. This expansion thus imposes pressure on the interior of the patient's uterus, acting to stanch blood flow from PPH. Further, the position of removal strand 106 (depicted as a loop of material, but could also be implemented as a single end strand) is outside of the patient, to allow for ease of subsequent removal of the PPH device 100.

Figure 7:
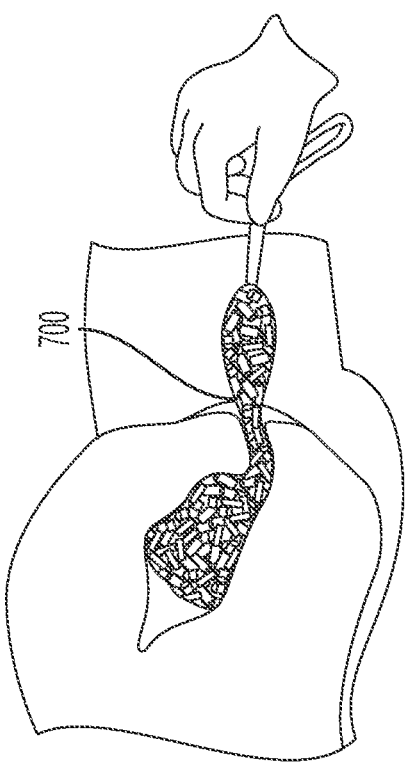
FIG. 7 is a diagram of the PPH device of FIG. 1 being removed from deployment, according to various embodiments.

FIG. 7 depicts how a deployed PPH device 100 may be removed from a patient, for example, once PPH has been successfully treated, or if the PPH device 100 needs to otherwise be changed or removed. As may be seen, in the example embodiment the removal strand 106 is grasped, preferably outside of the patient, and gently pulled away. In embodiments where removal strand 108 remains within the vaginal canal and does not extend outside the patient, the removal strand 108 may be grasped for removal within the vaginal canal, possibly by use of a tool such as a forceps. The removal strand 106 thus carries the used PPH device 100 out of the uterus, and out of the patient via the vaginal canal. PPH device 100, in embodiments, is a single use device and is subsequently discarded in an appropriate fashion. As can be seen in FIG. 7, PPH device 100 narrows around a central region 700 while passing out of the uterus and through the vaginal canal due to the positive Poisson's ratio, which results in PPH device 100 narrowing in cross section in response to being pulled along its length. This behavior was described above with respect to FIG. 1.

Figure 8:
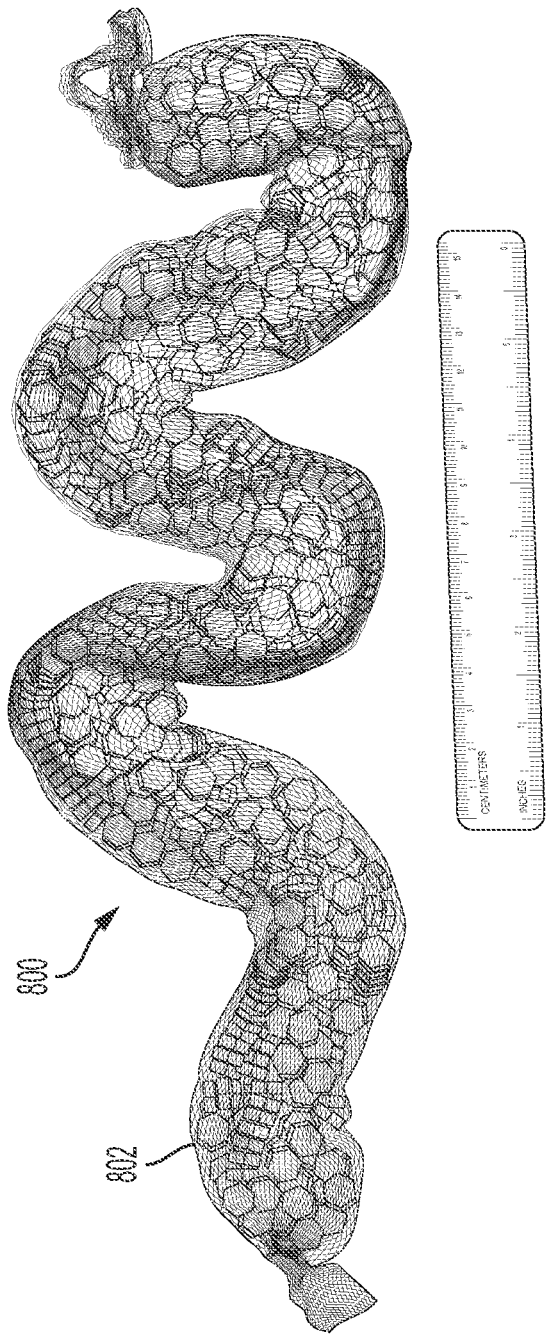
FIG. 8 is a diagram of a second example PPH device lacking a tip and a removal strand, according to various embodiments.

FIG. 8 depicts another possible embodiment of a PPH device 800. Similar to PPH device 100, PPH device 800 includes a mesh pouch 802 that is filled with one or more sponges, similar to pouch 102 and sponges 108. However, unlike PPH device 100, PPH device 800 lacks a tip or a removal strand. PPH device 800 may used with the applicator described above in substantially the same fashion, and may be installed pursuant to example method 400, except for leaving a removal strand outside of the uterus. PPH device 800 may be removed by alternative methods, such as grasping by a practitioner using a tool, as may be understood by a person skilled in the relevant art.

It will be appreciated that the configurations disclosed herein are exemplary in nature, and that these specific embodiments are not to be considered in a limiting sense, because numerous variations are possible. The subject matter of the present disclosure includes all novel and nonobvious combinations and subcombinations of the various systems and configurations, and other features, functions, and/or properties disclosed herein.

The following claims particularly point out certain combinations and subcombinations regarded as novel and nonobvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

EXAMPLES

Various example embodiments of the present disclosure follow:

Example 1 is a method for treating post-partum hemorrhaging (PPH), comprising placing a plurality of sponges disposed within a tubular pouch, into a patient's uterus, wherein each of the plurality of sponges is configured to expand in volume upon absorption of a fluid; the tubular pouch is comprised of a mesh material; the tubular pouch has a length and a cross section, and is elongated in its length relative to its cross section; and the plurality of sponges is configured to expand within the patient's uterus by absorbing blood.

Example 2 includes the subject matter of example 1, or another example herein, wherein placing a plurality of sponges disposed within a tubular pouch into a patient's uterus further comprises inserting a tubular applicator into a patient's vaginal canal so that a portion of the tubular applicator including the open end is disposed within the patient's uterus; injecting, using a plunger, the tubular pouch from the tubular applicator into the patient's uterus; and removing the tubular applicator, leaving the tubular pouch in the patient's uterus.

Example 3 includes the subject matter of example 1 or example 2, or another example herein, wherein the sponges are distributed within the tubular pouch at a density of at most 1.6 g of sponge per 2.5 cm of tubular pouch length.

Example 4 includes the subject matter of any of examples 1-3, or another example herein, further comprising, removing the tubular pouch from the patient's uterus.

Example 5 includes the subject matter of any of examples 1-4, or another example herein, wherein the tubular pouch further comprises a removal strand disposed upon an end of the tubular pouch; and removing the tubular applicator comprises leaving at least a portion of the removal strand outside of the patient's uterus.

Example 6 includes the subject matter of example 5, or another example herein, further comprising removing the tubular pouch from the patient's uterus by pulling upon the removal strand.

Example 7 is a device for treating post-partum hemorrhaging (PPH), comprising a tubular pouch having a first end and a second end distal from the first end, the tubular pouch comprised of a mesh material, the tubular pouch having a length and a cross section, wherein its length is elongated relative to its cross section; and a plurality of sponges disposed within the tubular pouch, each of the plurality of sponges configured to expand in volume upon absorption of a fluid; wherein the tubular pouch is configured to expand as at least a subset of the plurality of sponges expands upon absorption of the fluid.

Example 8 includes the subject matter of example 7, or another example herein, wherein the tubular pouch is filled with between 250 to 350 sponges.

Example 9 includes the subject matter of example 7 or 8, or another example herein, wherein the tubular pouch is sized so that the plurality of sponges disposed within the tubular pouch result in a sponge density no greater than 1.6 g of sponge for each 2.5 cm of the tubular pouch's length.

Example 10 includes the subject matter of any of examples 7-9, or another example herein, further comprising a sponge tip disposed upon the first end of the tubular pouch.

Example 11 includes the subject matter of example 10, or another example herein, wherein the sponge tip is comprised of uncompressed sponge.

Example 12 includes the subject matter of example 10 or 11, or another example herein, wherein the sponge tip comprises the same sponge material as the plurality of sponges.

Example 13 includes the subject matter of any of examples 7-12, or another example herein, further comprising a removal strand disposed upon the second end.

Example 14 includes the subject matter of any of claims 7-13, or another example herein, wherein the tubular pouch is configured to decrease in its cross section when its length increases.

Example 15 includes the subject matter of any of examples 7-14, or another example herein, wherein each of the plurality of sponges occupies a volume within the range of 0.7-7000 mm3 prior to absorption of liquid.

Example 16 is a system for treating post-partum hemorrhaging (PPH), comprising a PPH device comprised of an porous tubular pouch that has a length and a cross section, and is elongated in its length relative to its cross section; and a plurality of sponges disposed within the tubular pouch, each sponge comprised of a material that expands in volume upon absorption of a fluid; an applicator comprised of a hollow tube, sized to receive and enclose the PPH device; and a plunger configured to insert into the hollow tube.

Example 17 includes the subject matter of example 16, or another example herein, wherein the plunger is comprised of a handle, a hilt sized larger than a diameter of the applicator, and a plunger shaft configured to insert into the hollow tube, and wherein the hilt separates the handle from the plunger shaft.

Example 18 includes the subject matter of example 16 or 17, or another example herein, wherein the porous tubular pouch is comprised of a mesh material.

Example 19 includes the subject matter of example 18, or another example herein, wherein the mesh material is expandable.

Example 20 includes the subject matter of any of examples 16-19, or another example herein, wherein the plurality of sponges comprises between 250 to 350 sponges.

The invention claimed is:

1. A method for treating post-partum hemorrhaging (PPH), comprising placing a plurality of sponges disposed within a tubular pouch, into a patient's uterus, wherein:
   each of the plurality of sponges is configured to expand in volume upon absorption of a fluid;
   the tubular pouch is comprised of a mesh material;
   the tubular pouch has a length and a cross section, and is elongated in its length relative to its cross section;
   the plurality of sponges is configured to expand within the patient's uterus by absorbing blood; and
   a sponge tip enclosed within a compartment of the tubular pouch separate from the plurality of sponges or disposed on an outside of the tubular pouch.

2. The method of claim 1, wherein placing a plurality of sponges disposed within a tubular pouch into a patient's uterus further comprises:
   inserting a tubular applicator into a patient's vaginal canal so that a portion of the tubular applicator including its open end is disposed within the patient's uterus, wherein the sponge tip plugs the open end of the tubular applicator prior to ejection of the tubular pouch from the tubular applicator;
   injecting, using a plunger, the tubular pouch from the tubular applicator into the patient's uterus; and
   removing the tubular applicator, leaving the tubular pouch in the patient's uterus.

3. The method of claim 1, wherein the plurality of sponges are distributed within the tubular pouch at a density of at most 1.6 g of sponge per 2.5 cm of tubular pouch length.

4. The method of claim 1, further comprising, removing the tubular pouch from the patient's uterus.

5. The method of claim 2, wherein:
   the tubular pouch further comprises a removal strand disposed upon an end of the tubular pouch; and
   removing the tubular applicator comprises leaving at least a portion of the removal strand outside of the patient's uterus.

6. The method of claim 5, further comprising removing the tubular pouch from the patient's uterus by pulling upon the removal strand.

7. The method of claim 1, wherein a surface of the sponge tip is laminated or coated to prevent premature expansion of the sponge tip.

8. A device for treating post-partum hemorrhaging (PPH), comprising:
   a tubular pouch having a first end and a second end distal from the first end, the tubular pouch comprised of a mesh material, the tubular pouch having a length and a cross section, wherein its length is elongated relative to its cross section;
   a plurality of sponges disposed within the tubular pouch, each of the plurality of sponges configured to expand in volume upon absorption of a fluid; and
   a sponge tip enclosed within a compartment of the tubular pouch separate from the plurality of sponges or disposed on an outside of the tubular pouch;
   wherein the tubular pouch is configured to expand as at least a subset of the plurality of sponges expands upon absorption of the fluid.

9. The device of claim 8, wherein the tubular pouch is filled with between 250 to 350 sponges.

10. The device of claim 8, wherein the tubular pouch is sized so that the plurality of sponges disposed within the tubular pouch result in a sponge density no greater than 1.6 g of sponge for each 2.5 cm of the tubular pouch's length.

11. The device of claim 8, wherein the sponge tip is comprised of uncompressed sponge.

12. The device of claim 8, wherein the sponge tip comprises the same sponge material as the plurality of sponges.

13. The device of claim 8, wherein a removal strand is disposed upon the second end.

14. The device of claim 8, wherein the tubular pouch is configured to decrease in its cross section when its length increases.

15. The device of claim 8, wherein each of the plurality of sponges occupies a volume within the range of 0.7-7000 $mm^3$ prior to absorption of liquid.

16. The device of claim 8, wherein the tubular pouch has a flat width of 1-15 cm and length from 25-150 cm.

17. The device of claim 8, wherein a surface of the sponge tip is laminated or coated to prevent premature expansion of the sponge tip.

18. A system for treating post-partum hemorrhaging (PPH), comprising:
   a PPH device comprised of:
      a porous tubular pouch that has a length and a cross section, and is elongated in its length relative to its cross section;
      a plurality of sponges disposed within the tubular pouch, each sponge comprised of a material that expands in volume upon absorption of a fluid; and
      a sponge tip enclosed within a compartment of the tubular pouch separate from the plurality of sponges or disposed on an outside of the tubular pouch;
   an applicator comprised of a hollow tube, sized to receive and enclose the PPH device; and
   a plunger configured to insert into the hollow tube.

19. The system of claim 18, wherein the plunger is comprised of a handle, a hilt sized larger than a diameter of the applicator, and a plunger shaft configured to insert into the hollow tube, and wherein the hilt separates the handle from the plunger shaft.

20. The system of claim 18, wherein the porous tubular pouch is comprised of a mesh material.

21. The system of claim 20, wherein the mesh material is expandable.

22. The system of claim 18, wherein the plurality of sponges comprises between 250 to 350 sponges.

23. The system of claim 18, wherein a surface of the sponge tip is laminated or coated to prevent premature expansion of the sponge tip.

* * * * *